United States Patent [19]

Kurtz et al.

[11] Patent Number: 4,550,722
[45] Date of Patent: Nov. 5, 1985

[54] ORTHOPEDIC FOOT SPLINT WITH SWIVEL AND STOP

[75] Inventors: Robert J. Kurtz, New York; Joseph LiCausi, Port Jefferson Station, both of N.Y.

[73] Assignee: BioResearch Inc., Farmingdale, N.Y.

[21] Appl. No.: 557,215

[22] Filed: Dec. 2, 1983

Related U.S. Application Data

[63] Continuation-in-part of Ser. No. 531,583, Sep. 13, 1983, Pat. No. 4,481,940, which is a continuation of Ser. No. 358,531, Mar. 16, 1982, abandoned.

[51] Int. Cl.[4] .............................................. A61F 3/00
[52] U.S. Cl. .............................................. 128/80 A
[58] Field of Search ................... 128/80 A, 80 J, 88, 128/87 R

[56] References Cited

U.S. PATENT DOCUMENTS

| | | | |
|---|---|---|---|
| 2,963,020 | 12/1960 | Moran | 128/80 A |
| 3,892,231 | 7/1975 | Tummillo | 128/80 A |
| 4,249,523 | 2/1981 | Bidwell | 128/80 A |
| 4,263,901 | 4/1981 | Nichols | 128/80 A |
| 4,303,065 | 12/1981 | Ericson | 128/80 A |

Primary Examiner—John D. Yasko

[57] ABSTRACT

An orthopedic foot splint which is attached to the shoes of a user to correct for a toe-in or toe-out condition is disclosed. The foot splint includes a pair of shoe engaging plates and an elongate connecting mechanism. A swivel is provided between the shoe engaging plate and the end of the connecting mechanism so that the shoe of the user can rotate about a vertical axis. The swivel includes a stop which is adjustable to restrict the movement of the swivel so that the toe or heel of the shoe swivels either towards or away from the connecting mechanism from an initial position where the longitudinal axis of the shoe engaging plate is substantially perpendicular to the longitudinal axis of the connecting mechanism. A mechanism for locking the shoe engaging plate against swiveling movement is also provided. The connecting mechanism can include two bars, a central pivot, a central hinge, and lateral hinges. At least one bar is also laterally extendable according to the needs of the user. In place of a bar, a pair of parallelogram links with a tether can be provided. The central pivot can also be provided with a stop to prevent rotation of one foot in front of or in back of the other.

10 Claims, 8 Drawing Figures

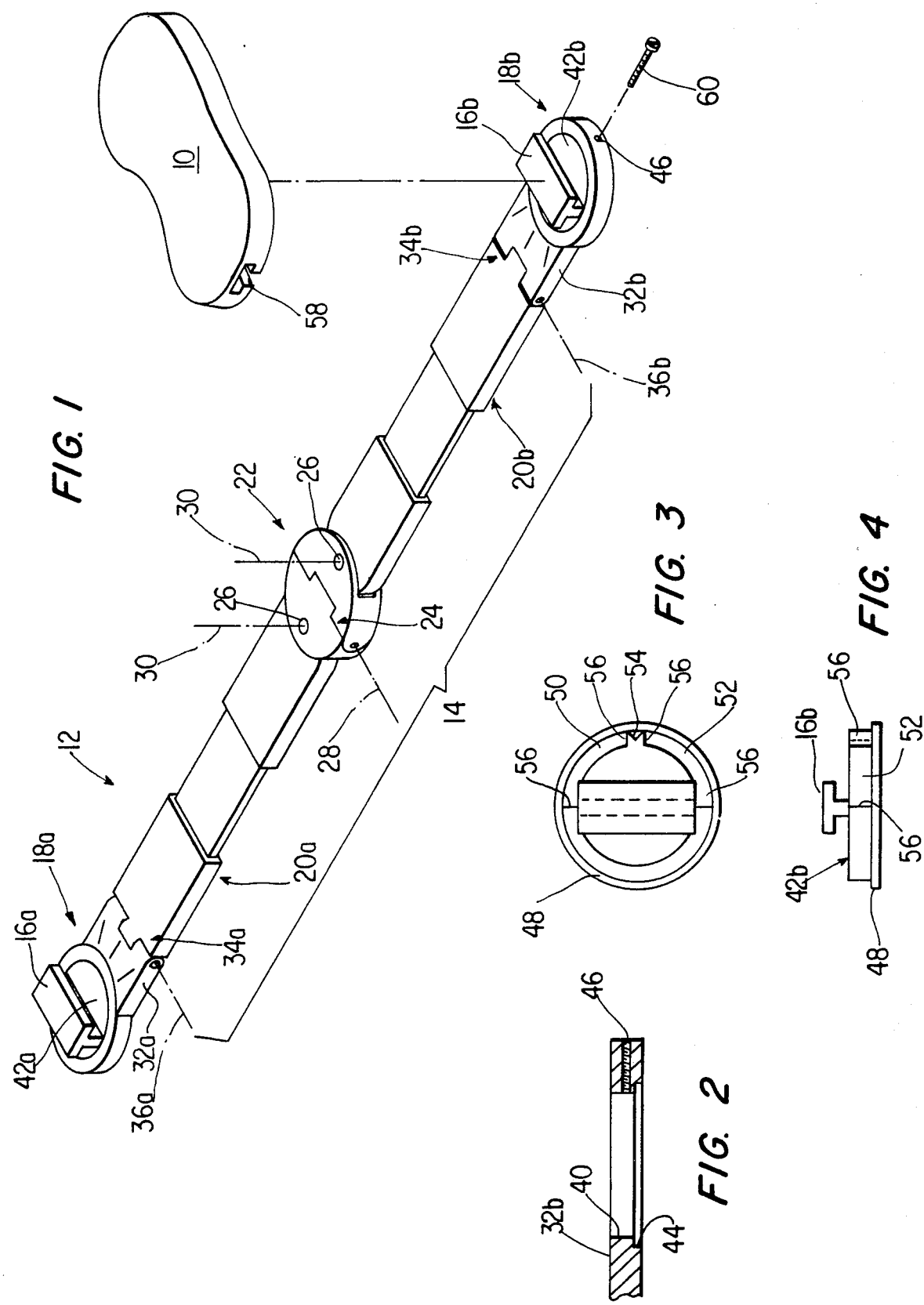

ORTHOPEDIC FOOT SPLINT WITH SWIVEL AND STOP

REFERENCE TO RELATED APPLICATIONS

This application is a continuation-in-part of application Ser. No. 531,583 filed Sept. 13, 1983, now U.S. Pat. No. 4,481,940, issued Nov. 13, 1984 which is a continuation of abandoned application Ser. No. 358,531 filed Mar. 16, 1982 now abandoned.

FIELD OF THE INVENTION

This invention relates generally to the field of orthopedic splints which correct for toe-in and toe-out, and more particularly to such a device which corrects one foot or both while allowing some freedom of movement for a normal or abnormal foot.

BACKGROUND OF THE INVENTION

In general, an orthopedic foot splint is useful in correcting bone deformities, particularly in children, by holding the patient's feet at an appropriate corrective angle. Thus, if a patient's feet are abnormally toed-in, it is recommended that the patient wear a splint for a specified period which will hold the feet in a corrective toed-out position. A common type of prior art devices, as disclosed in U.S. Pat. Nos. 2,920,620 (Rogers), 4,040,416 (Zentman), and 4,008,129 (DiGiulio), includes a pair of shoes mounted on a flat bar. The shoes is these devices are adjustable on the bar to provide a variety of different toe-in and toe-out angles, but are not otherwise adjustable. Unfortunately, these prior art devices are extremely uncomfortable to the patient as they maintain the feet in almost rigid positions. Even the patent to Zentman which includes a flexible spacer bar to allow a slight amount of vertical movement does little to alleviate this problem. In addition, the patient cannot move except by hopping, which in dangerous and perhaps impossible for young children to perform.

To overcome this almost total lack of mobility and extreme discomfort, prior art devices have been proposed which do allow some movement as well. For instance, in U.S. Pat. No. 2,963,020 (Moran) and No. 4,303,065 (Ericson), a device is disclosed which comprises a separate member attached to each shoe of the patient which members are connected by parallelogram links. These linkages are pivotally attached to each shoe member and this allows movement of the feet both upwards and downwards, and forwards and rearwards. In addition, the length of the linkages is manually adjustable in the former patent. U.S. Pat. No. 3,487,829 (Barnett) also discloses parallelogram links connecting shoe engaging members. In this device, the parallelogram links are attached to the shoe engaging members by ball and socket joints. This device also allows the feet to move forwards and backwards, and upwards and downwards, as well as allowing the ends of the shoes to tilt upwards or downwards somewhat.

In U.S. Pat. No. 4,249,523 (Bidwell), an adjustable orthopedic foot splint to which a pair of shoes is attached is disclosed which maintains a desired angle between the shoes but which otherwise allows virtually full freedom of movement of the shoes.

Disclosed in pending U.S. application entitled "Adjustable Orthopedic Shoe For A Foot Splint", Ser. No. 339,058, filed Jan. 13, 1982, now abandoned and refiled as Ser. No. 579,584 on Feb. 13, 1984 is an orthopedic shoe which is preferably used where the toe of the user is required to be adjusted relative to the heel, and where a foot splint is used to adjust the feet of the user. Disclosed in the pending U.S. application entitled "Orthodpedic Foot Splint", Ser. No. 343,555, filed Jan. 28, 1982, now U.S. Pat. No. 4,412,536, issued Nov. 1, 1983 is an adjustable orthopedic foot splint which allows virtually full freedom of movement of the feet except for an undesired movement of one foot of the user in front of or too close to the other foot. This is accomplished by using parallelogram links with a tether attached therebetween. Both of these applications are assigned to the assignee of the present application, and are herein incorporated by reference.

SUMMARY OF THE INVENTION

In accordance with the present invention, an orthopedic foot splint is provided for correcting bone deformities by holding the foot to be corrected at a corrective angle. The foot splint of the present invention includes a pair of shoe engaging plates and an elongate connecting means interconnecting the shoe engaging plates. A swivel means is provided between the connecting means and the shoe engaging plates so that the shoe engaging plates can swivel about a vertical axis. A stop means is provided in the swivel means so that the toe or heel of a respective shoe can only swivel either towards or away from the connecting means from an initial position which is substantially perpendicular to the longitudinal axis of the connecting means. With such a device, the shoe engaging plate of the foot requiring correction is restricted from movement in the undesired direction, for example toe-in. However, by use of the selected stop means, the foot to be corrected is allowed a swivel movement to the toe-out position. The other foot, which is frequently without a defect and needs no correction, is also allowed some freedom of movement. Where the foot to be corrected is prevented from toeing-in, the normal foot is allowed by the swivel means and stop means to swivel to the toe-in position (although toe-out must be prevented so that toe-in of the other, defective foot, can be prevented).

In the preferred embodiment of the present invention, a lock means is further provided to lock the shoe engaging plate in position and prevent swiveling. The connecting means also includes two bars, having a central pivot, a central hinge, and lateral hinges so that desired movements of the feet are not prevented. Preferably, at least one of the bars also is freely extensible so that the longitudinal length of the connecting means is easily varied according to the needs of the user.

In another preferred embodiment of the present invention, the connecting means includes at least one pair of parallelogram links. These parallelogram links include a tether attached at an angle to the links so that pivoting in the horizontal plane beyond a predetermined angle can be prevented. A bar and a pair of parallelogram links can be provided together with a central hinge and lateral hinges at each end. The parallelogram links can also be provided with a block means to prevent pivoting beyond a predetermined angle on either side of a horizontal line perpendicular to the longitudinal axis of the shoe engaging plate. Two pairs of parallelogram links can also be used.

The swivel means preferably comprises a circular aperture in the shoe engaging plate and a circular disc rotatably mounted in the aperture. By providing two cutouts adjacent one another on the circular disc, a screw mounted to the shoe engaging plate which extends into the cutouts can be used to appropriately limit the rotation of the circular disc to the length of the cutout and the corresponding orientation of the foot of the user.

In still another preferred embodiment, the central pivot is provided with the cutouts and a screw mounted relative to one of the cutouts. The screw is used to appropriately limit rotation of the central pivot in the horizontal plane beyond a predetermined angle.

Other features, objects, and advantages of the present invention are stated in or apparent from the detailed description of the presently preferred embodiments of the invention found hereinbelow.

BRIEF DESCRIPTION OF THE DRAWINGS

FIG. 1 is a perspective view of an orthopedic foot splint according to the present invention.

FIG. 2 is a cross-sectional plan view of the base plate of the swivel depicted in FIG. 1.

FIG. 3 is a top plan view of the circular disc of the swivel depicted in FIG. 1.

FIG. 4 is a front plan view of the circular disc depicted in FIG. 3.

DETAILED DESCRIPTION OF THE PREFERRED EMBODIMENTS

Figure 5:
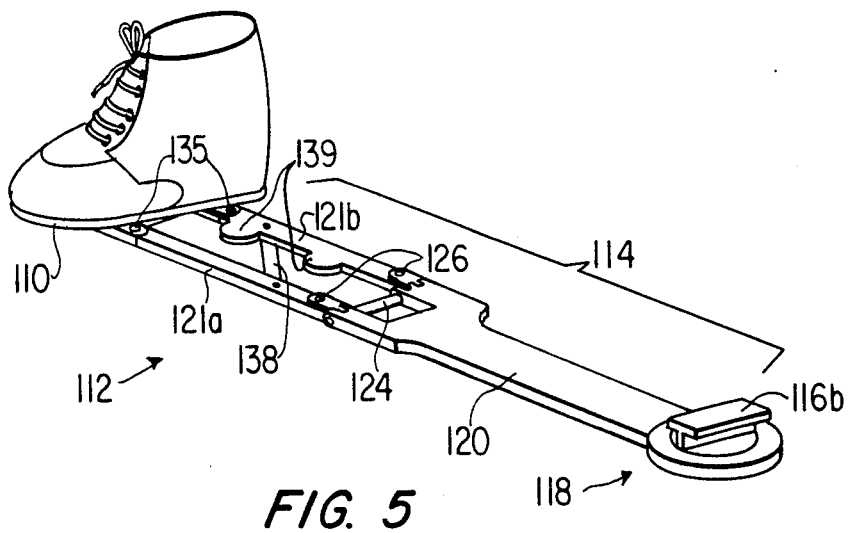
FIG. 5 is a perspective view of an alternative embodiment of an orthopedic foot splint according to the present invention.
Figure 6:
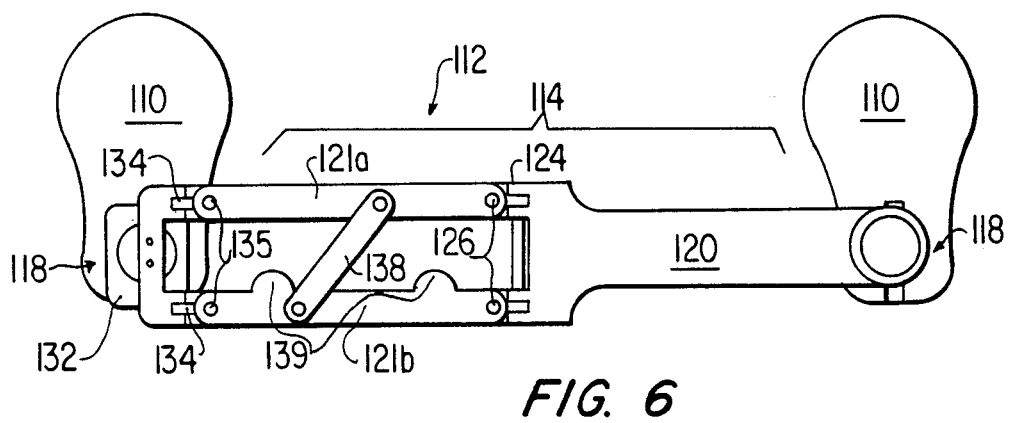
FIG. 6 is a bottom plan view of the orthopedic foot splint depicted in FIG. 5.

With reference now to the drawings in which like numerals represent like elements throughout the several views, a presently preferred embodiment of the present invention is depicted in FIG. 1 along with a shoe plate 10 to which the shoe of the user is attached. A preferred type of shoe is disclosed in the pending U.S. application disclosed above entitled "Adjustable Orthopedic Shoe For A Foot Splint", which is herein incorporated by reference. Orthopedic foot splint 12 includes a connecting means 14, a pair of shoe engaging plates 16a and 16b and a pair of swivel means 18a and 18b.

In the preferred embodiment, connecting means 14 includes two bars 20a and 20b which are interconnected by a joint 22. Preferably, each bar 20a and 20b is freely extensible in the longitudinal direction. This is easily provided by forming bars 20a and 20b from telescoping sections. Conveniently, a stop (not shown) is also provided to prevent the telescoping sections from being pulled apart. Joint 22 includes a central hinge means 24 as well as a central pivot means 26 so that two planes of motion are possible with bars 20a and 20b. Thus, bars 20a and 20b can pivot relative to one another about axis 28 which is horizontal and substantially perpendicular to the longitudinal axis of connecting means 14. In addition, bars 20a and 20b can pivot in a horizontal plane relative to one another around axes 30 which are vertical. The opposite ends of bars 20a and 20b are connected to a base plate 32a and 32b by lateral hinge means 34a and 34b. In this manner, base plates 32a and 32b can pivot in a vertical plane relative to bars 20a and 20b about axes 36a and 36b, respectively, which are parallel to axis 28.

As shown in greater detail in FIGS. 2, 3, and 4, swivel means 18b includes a circular aperture 40 located in base plate 32b and a circular disc 42 which is received in circular aperture 40. As shown in FIG. 2, circular aperture 40 includes a shoulder recess 44 and a threaded bore 46. As shown in FIGS. 3 and 4, circular disc 42 includes a lower shoulder 48. When circular disc 42 is inserted in circular aperture 40 of base plate 32b, shoulder 48 engages shoulder recess 44. In this manner, circular disc 42 is rotatably mounted in base plate 32b.

Circular disc 42 also includes two cutout portions 50 and 52 which are approximately 90° in length around the circumference of circular disc 42. Located between cutout portions 50 and 52 is a small notch 54. The end faces of cutout portions 50 and 52 form stops 56 whose function will be disclosed subsequently. Mounted to the top of circular disc 42 is shoe engaging plate 16b which has a substantially T-shaped cross section. Referring again to FIG. 1, it can be seen that shoe engaging plate 16b is received in a correspondingly shaped slot 58 in shoe plate 10. A suitable mechanism is then provided to lock shoe plate 10 to shoe engaging plate 16b. Also shown in FIG. 1 is a screw 60 which is received in threaded bore 46 of base plate 32b. By adjusting circular disc 42 appropriately, the end of screw 60 can be located in either of cutout portions 50 and 52 or in notch 54. When the end of screw 60 is located in notch 54, circular disc 42 cannot rotate relative to base plate 32b. However, when the end of screw 60 is located in either of cutout portions 50 and 52, circular disc 42 can rotate approximately 90° relative to base plate 32b until the end of screw 60 contacts stops 56. It should be appreciated that shoe plate 10 extends longitudinally beyond both ends of shoe engaging plate 16b so that circular disc 42 is trapped in base plate 32b by shoulder 48 and the bottom of shoe plate 10.

In operation, orthopedic foot splint 12 functions in the following manner. Initially, it must be determined what condition exists in the patient and the appropriate corrective position of the foot which is desired. For example, where the right foot of the patient is toed-in, it is desired to hold the right foot in a substantially parallel or toed-out position. However, where the left foot is normal and requires no corrective action, it is desired to provide as much freedom as possible to the left foot. Therefore, circular disc 42b is initially adjusted so that the end of screw 60 is located in cutout portion 50. Similarly, the end of the screw is swivel means 18a is located in one of the corresponding cutouts in circular disc 42a. In this manner, the right foot is prevented by the movement of circular disc 42b from moving to the toed-in position (i.e., always maintained in the toed-out position), and the right foot is allowed freedom of movement in the toed-out position. Similarly, the other, normal foot is allowed approximately 90° of free movement in either the toed-in or toed-out position (preferably, the toed-in position).

By use of orthopedic foot splint 12, an approximately normal walking movement is allowed while the right foot of the user is maintained in the toed-out position. Thus, during walking, as the right foot is brought forward relative to the left foot, the right foot is maintained in the toed-out position by swivel means 18b even though the right foot can be raised or lowered due to lateral hinge means 34a and 34b and central hinge means 24. The bringing forward of the right foot is allowed by the pivoting of bars 20a and 20b relative to one another due to central pivot means 26. The separation of the feet of the user is easily varied due to the telescoping parts of bars 20a and 20b so that pressure on the knee and hip from an improper separation is avoided.

If it is desired to prevent either one of the feet from obtaining a toed-in or a toed-out position, it is also possible to adjust the end of screw 60 so that the end is received in notch 54. In this manner, the respective foot is then maintained between the toed-out and toed-in position. Obviously, both feet could also be maintained in either the toed-in or toed-out position if necessary.

Besides having a toed-in or toed-out condition, it is frequently found that the patient in addition has difficulty with one foot rotating in an inward direction in front of the other foot while walking. While orthopedic foot splint 12 does not correct for this condition, orthopedic foot splint 112 does correct for this condition. Orthopedic foot splint 112 is somewhat similar to the orthopedic foot splint disclosed in the pending U.S. application referred to above entitled "Orthopedic Foot Splint", which application is herein incorporated by reference. In this embodiment, orthopedic foot splint 112 includes a connecting means 114 comprised of a bar 120 and a pair of parallelogram links 121a and 121b. Orthopedic foot splint 112 also includes swivel means 118a and 118b and shoe engaging plates such as 116b. Shoe plates 110 are also shown.

In this embodiment, bar 120 is attached to parallelogram links 121a and 121b by a central hinge means 124. In addition, parallelogram links 121a and 121b are attached to central hinge means 124 by central pivot means 126. A lateral hinge means 134 is also provided to attach parallelogram links 121a and 121b to base plate 132. Attached between links 121a and 121b at an angle thereto is a tether 138. Tether 138 prevents links 121a and 121b from pivoting beyond a predetermined angle. As depicted, tether 138 prevents links 121a and 121b from pivoting forward, but allows pivoting rearward.

In operation, orthopedic foot splint 112 functions in a manner similar to orthopedic foot splint 12. The feet of the user are restrained in a similar manner, and similar freedoms of movement are allowed. However, orthopedic foot splint 112 prevents one foot (the right foot) from moving in front of the other foot. During walking, as the right foot is moved forward, parallelogram links 121a and 121b pivot about central pivot means 126 and a lateral pivot means 135. However, as the right foot is brought laterally adjacent to the left foot, tether 138 prevents parallelogram links 121a and 121b from pivoting in a horizontal plane any further. Therefore, the right foot cannot pivot any further forward as well and is prevented from crossing in front of the left foot. The left foot is then free to move forward in a relatively normal manner. In order to prevent the left foot from moving too far forward, blocks 139 are located on parallelogram link 121a. It should be noted that where orthopedic foot splint 112 is being used to prevent toe-in of the right foot, swivel means 118 of the left foot must be adjusted so that either toe-in (preferably) or no rotating movement is allowed. If swivel means 118 of the left foot is adjusted so that toe-out is provided, this would allow the right foot to cross over towards the left foot during forward movement of the right foot.

Figure 7:
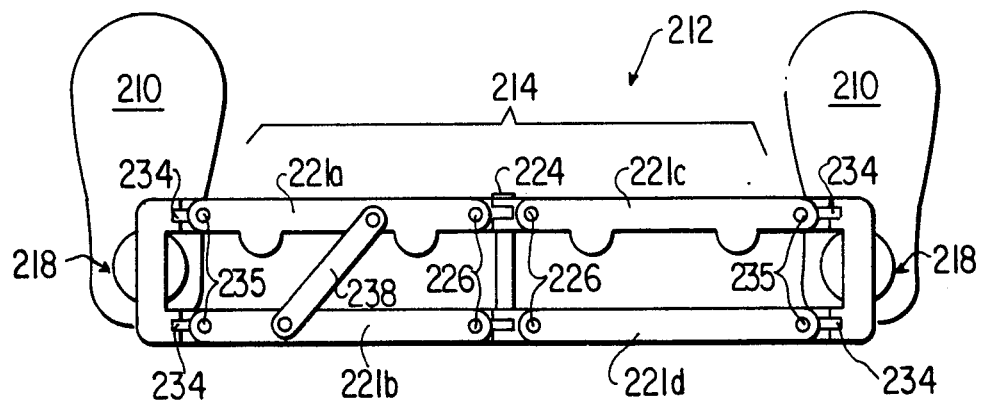
FIG. 7 is a bottom plan view of still another alternative embodiment of an orthopedic foot splint according to the present invention.

Depicted in FIG. 7 is a modified orthopedic foot splint 212 which is similar to orthopedic foot splint 112. In this embodiment, two pairs of parallelogram links 221a, 221b, 221c, and 221d are provided. Connecting the two pairs of parallelogram links are a central hinge means 224, and a central pivot means 226. At the opposite ends of the two pairs of parallelogram links are lateral hinge means 234 and lateral pivot means 235. Orthopedic foot splint 212 is provided with suitable swivel means 218 and shoe plates 210. Connecting one pair of parallelogram links, such as parallelogram links 221a and 221b, is a tether 238.

The operation of foot splint 212 is similar to the operation of foot splint 112. However, with foot splint 212, only the swivel means 218 of the foot to be corrected need be adjusted to prevent the undesired positioning of that foot. The other swivel means 218 can be permitted to swivel as desired, for example by removing the screw which limits movement. In this manner, virtually free movement as desired of the normal foot is allowed while the undesired movement of the foot to be corrected is prevented. As with foot splint 112, during walking, the foot to be corrected can only be brought up to a position laterally opposite the normal foot.

Figure 8:
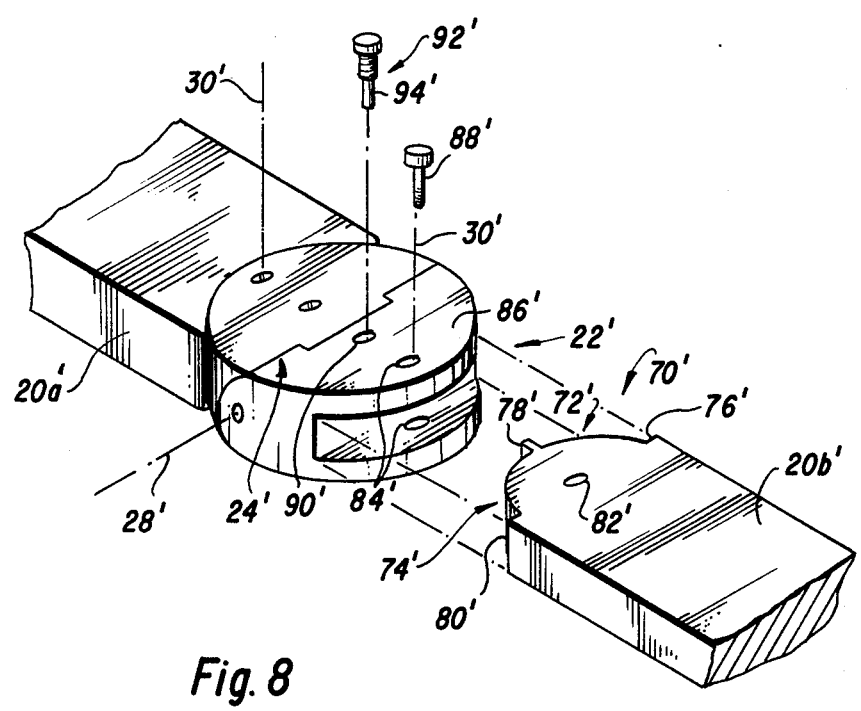
FIG. 8 is a perspective view of an alternative embodiment of the central pivot depicted in FIG. 1.

Depicted in FIG. 8 is an alternative embodiment of a joint 22' which can be used in place of joint 22 of orthopedic foot splint 12 depicted in FIG. 1. As with joint 22, joint 22' connects bars 20a' and 20b' and has a central hinge means 24'. A central pivot means 26' on either side of central hinge means 24' is also provided. In this manner, joint 22' allows bars 20a' and 20b' to pivot relative to one another vertically about axis 28' and horizontally about axes 30'. However, instead of having a semi-circular end as in joint 22, bars 20a' and 20b' have an end 70' as shown on bar 20b'.

End 70' of bar 20b' would be semi-circular except that cutout portions 72' and 74' are provided between stops 76', 78', and 80'. As shown, end 70' is also provided with an aperture 82' which aligns with apertures 84' provided in base 86' of joint 22'. A pivot screw 88' is then received through apertures 82' and 84' to pivotally mount bar 20b' to joint 22'.

Base 86' is further provided with a threaded aperture 90' in which a stop screw 92' is threadably received. Aperture 90' is positioned such that the lower end 94' of stop screw 92' is located in either cutout 72' or 74' when bar 20b' is pivotally mounted to base 86' by pivot screw 88'.

In operation, joint 22' is used to prevent one foot from ever moving in front of or in back of the other foot when joint 22' is used in place of joint 22 in orthopedic foot splint 12. For example, the following procedure is used to prevent one foot from moving in front of the other foot. Initially, swivel means 18a and 18b are adjusted to maintain both feet in the toed-out position. Next, stop screw 92' is inserted in cutout portion 74' of bar 20b'. In a similar manner, a set screw is inserted in the corresponding cutout portion of bar 20a'. When this is accomplished, bars 20a' and 20b' cannot pivot forward of one another, but instead can only up to a position where bars 20a' and 20b' are parallel.

In order to walk, the user must alternately pivot one foot to a greater toed-out position and then move the other foot forward. For example, where the feet are initially parallel to one another, the left foot is initially toed-out to a greater degree. This allows bar 20a' to pivot forward of the left foot and hence bar 20b' and the right foot can pivot forward. However, it should be noted that the right foot cannot pivot in front of the left foot as the right foot can only assume a position approximately parallel to the left foot. After this is accomplished, the right foot is toed out further allowing the left foot to similarly move to a position parallel to the right foot. With this two part shuffling motion, the user can walk forward.

In addition to preventing one foot from pivoting in front of the other foot, joint 22' is also used in a like manner to prevent one foot from pivoting behind the other foot. In such a situation, swivel means 18a and 18b are adjusted to maintain both feet in the toed-in position. Stop screw 92' is then inserted in cutout portion 72' of bar 206' and bar 20a' is similarly restricted. Thus, bars 20a' and 20b' cannot pivot rearwards of one another. In walking the user must alternately pivot one foot to a greater toed in position and then move the other foot rearwardly, but never behind the other foot.

It should be appreciated that the precise location of stops 76', 78', and 80' can be varied to vary the amount of movement allowed. In addition, stop 78' does not have to be placed midway between stop 76' and 78'. In addition, it would also be possible to locate a removable stop member is cutaway portion 72' or 74' to further temporarily restrict the movement of bars 20a' or 20b'. The removable stop member could be removably attached to end portion 94' of stop screw 92'.

Instead of shoe engaging plate 16 as depicted, a number of other shoe engaging plates could be provided. For example, in U.S. Pat. No. 4,249,523 (mentioned above) which patent is hereby incorporated by reference, a shoe engaging plate and an associated plate pivot means could be provided with the present invention to allow rotation of the foot of the user about an axis that is parallel to the longitudinal axis of the connecting means. In addition, the above mentioned patent also discloses a means for exactly positioning the angle of the foot which could be used in conjunction with the swivel means of the present invention.

Thus, while the present invention has been described with respect to exemplary embodiments thereof, it will be understood by those of ordinary skill in the art that variations and modifications can be effected within the scope and spirit of the invention.

We claim:

1. An orthpedic foot splint which is attached to the shoes of a user comprising:
   a pair of shoe engaging plates, each said plate having a longitudinal axis approximately parallel to the longitudinal axis of the shoe which is attachable thereto;
   an elongate connecting means for horizontally interconnecting said pair of shoe engaging plates, said connecting means including
   (a) two elongate sections, one end of each said elongate section being connected to a respective shoe engaging plate,
   (b) longitudinal pivot means comprising the connection between at least one elongate section and shoe engaging plate, and
   (c) a central joint means including a longitudinal hinge to permit said sections to move with respect to each other in a plane perpendicular to the axis of said hinge, pivot means disposed perpendicular to said longitudinal hinge for permitting angular movement of one of said elongate sections with respect to the other elongate section on an axis vertically disposed with respect to the axis of said longitudinal hinge, and a restricting means for preventing angular movement of one of said elongate sections beyond a predetermined angle with respect to the longitudinal axis of the other of said elongate sections whereby one shoe engaging plate is prevented from moving in front of the other shoe engaging plate while permitting the other shoe engaging plate to move in front of said one shoe engaging plate.

2. An orthopedic foot splint as claimed in claim 1 and further including a swivel means provided between said connecting means and at least one of said shoe engaging plates for allowing said shoe engaging plate to swivel about a vertical axis with respect to said connecting means, said swivel means including a stop means for selectively restricting the movement of said swivel means such that the toe or heel of the respective shoe can only swivel toward or away from said connecting means from an initial position where the longitudinal axis of said shoe engaging plate is approximately perpendicular to said longitudinal axis of said connecting means.

3. An orthopedic foot splint as claimed in claim 1 wherein said two elongate sections are two straight bars.

4. An orthopedic foot splint as claimed in claim 2 wherein said two elongate sections are two straight bars.

5. An orthopedic foot splint as claimed in claim 3 wherein at least one of said elongate sections includes an extending means for freely allowing the longitudinal length to vary according to the needs of the user.

6. An orthopedic foot splint as claimed in claim 4 wherein at least one of said elongate sections includes an extending means for freely allowing the longitudinal length to vary according to the needs of the user.

7. An orthopedic foot splint as claimed in claim 1 wherein said restricting means prevents angular movement of one of said elongate sections longitudinally ahead of the other.

8. An orthopedic foot splint as claimed in claim 2 wherein said restricting means prevents angular movement of one of said elongate sections longitudinally ahead of the other.

9. An orthopedic foot splint as claimed in claim 1 wherein said restricting means prevents angular movement of one of said elongate sections longitudinally in back of the other.

10. An orthopedic foot splint as claimed in claim 2 wherein said restricting means prevents angular movement of one of said elongate sections longitudinally in back of the other.

* * * * *